United States Patent [19]

Del Pesco

[11] B 4,001,260
[45] Jan. 4, 1977

[54] SYNTHESIS OF AROMATIC AMINES BY REACTION OF AROMATIC COMPOUNDS WITH AMMONIA

[75] Inventor: Thomas W. Del Pesco, Wilmington, Del.

[73] Assignee: E. I. Du Pont de Nemours and Company, Wilmington, Del.

[22] Filed: Dec. 19, 1973

[21] Appl. No.: 429,027

[44] Published under the second Trial Voluntary Protest Program on March 23, 1976 as document No. B 429,027.

[52] U.S. Cl. .................. 260/296 R; 260/288 R; 260/294.9; 260/295 AM; 260/465 E; 260/558 A; 260/559 A; 260/571; 260/575; 260/581
[51] Int. Cl.$^2$ .................................... C07C 85/02
[58] Field of Search ................. 260/581, 296 R

[56] References Cited
UNITED STATES PATENTS 3,231,616  1/1966  Jones .................... 260/581

FOREIGN PATENTS OR APPLICATIONS 553,988  3/1958  Canada .................. 260/581

OTHER PUBLICATIONS

Squire, "Chem. Abstracts," vol. 76, pp. 338–339, Abstract Nos. 24890k, 24891m, 24892n, (1972).
Squire, "Chem. Abstracts", vol. 78, p. 328, Abstract No. 3941d, (1973).

*Primary Examiner*—Elbert L. Roberts
*Assistant Examiner*—S. P. Williams

[57] ABSTRACT

An improved process is provided for producing an aromatic amine from ammonia and an aromatic compound which comprises reacting the aromatic compound with ammonia at a temperature of from about 150° C. to about 500° C. and at a pressure of from about 10 to about 1000 atmospheres in the presence of a conditioned nickel/nickel oxide/zirconium oxide cataloreactant which has been treated with ammonia prior to introduction of the cataloreactant to the amination reactants.

6 Claims, No Drawings

SYNTHESIS OF AROMATIC AMINES BY REACTION OF AROMATIC COMPOUNDS WITH AMMONIA

BACKGROUND OF THE INVENTION

As is well known, arylamines have been made in a variety of ways including reduction of the corresponding nitro compound, reaction of a chloro compound with ammonia either along or with catalysts such as copper salts, reaction of phenols with ammonia and zinc chloride at an elevated temperature and by the well-known Hofmann amide rearrangement with a hypohalite or halogen and a base. For some time, more direct methods of producing arylamines have been sought.

More recently, Canadian Pat. No. 553,988 issued on Mar. 4, 1958, to Thomas describes a one-step process for the production of aromatic amines. One embodiment comprises contacting a mixture of benzene, ammonia and oxygen in the vapor phase with a platinum catalyst maintained at a temperature of about 1000°C. In another embodiment, a mixture of benzene and ammonia is contacted in the vapor phase with a reducible metal oxide such as nickel oxide at a temperature of about 100°C. to 1000°C. The benzene is directly converted to aniline as represented by the equation $$C_6H_6 + NH_3 + MO \rightarrow C_6H_5NH_2 + H_2O + M,$$

wherein M represents the metal and MO represents the oxide thereof.

U.S. Pat. No. 2,948,755 issued on Aug. 9, 1960 to Louis Schmerling describes the preparation of aromatic amines by reacting an aromatic compound such as benzene with anhydrous ammonia in the presence of a compound of a group VI-B metal such as molybdenum, tungsten or chromium and a promoter consisting of an easily reducible metallic oxide such as an oxide of copper, iron, nickel, silver or gold at a temperature in the range from about 200° to 600°C. The easily reducible metallic oxide is stated to perform as a hydrogen acceptor to thus remove the by-product hydrogen produced, causing the reaction to proceed in the desired direction.

An earlier reference, J. B. Wibaut, Berichte, 50, 541–6 (1917), reported the synthesis of aniline by passing benzene and ammonia through an iron tube packed with reduced nickel, iron and asbestos at a temperature in the range of 550° to 600°C.

While the methods of these references do provide direct processes for the production of aromatic amines, they do so in low conversions and yields of the aromatic compound to aromatic amines.

In an attempt to obviate these problems, it has been proposed to carry out the reaction between ammonia and the aromatic compound in the presence of a conditioned nickel/nickel oxide/zirconium oxide cataloreactant, so named because it acts as a catalyst as well as a reactant in the direct amination of an aromatic compound with ammonia. Prior to use in the reaction the cataloreactant is conditioned. That is, the nickel oxide component of the cataloreactant is partically reduced to elemental nickel in a reducing atmosphere such as hydrogen. The elemental nickel formed by this process is partially oxidized back to nickel oxide in an oxidizing atmosphere such as oxygen, air or water. In spite of the improved results achieved using such catalysts, the demands of production make it necessary to continue the search for still better catalysts which yield still higher conversions.

SUMMARY OF THE INVENTION

In accordance with this invention, improved conversions of aromatic compounds to aromatic amines can be obtained when the aromatic compound is reacted with ammonia at a temperature of from about 150°C. to about 500°C. at a pressure of from about 10 to about 1000 atmospheres in the presence of a cataloreactant which has been conditioned and subsequently treated with ammonia immediately before being introduced to the ammonia and aromatic compound reactants.

DESCRIPTION OF EMBODIMENTS OF THE INVENTION

A. The Cataloreactant

The reaction between the aromatic compound and ammonia is an equilibrium reaction represented by the following equation using benzene as an example:

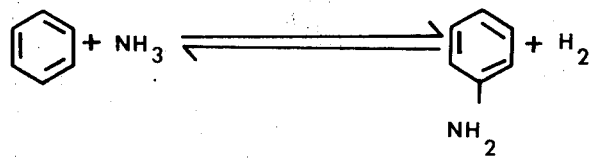

The mole ratio of ammonia/aromatic compound is preferably from 0.1 to 20, most preferably from 1.0 to 10, although any desired ratios may be employed.

The cataloreactants of the invention are nickel/nickel oxide/zirconium oxide compositions which function both as catalysts and as reactants in the amination of the aromatic compound. Specifically, the elemental nickel catalyzes the reaction between the aromatic compound and ammonia while the nickel oxide component is the reactant. The nickel oxide is reduced to elemental nickel by the hydrogen formed during the reaction between the aromatic compound and ammonia. The zirconium oxide component is a support-promoter which enhances the catalytic properties of the cataloreactant and prevents reduced nickel crystallite coalescence by physically separating the crystallites. The preferred mole ratio of nickel to nickel oxide is 0.001 to 10, most preferably 0.01 to 1. The mole ratio of the total nickel in the form of nickel and nickel oxide in the cataloreactant to zirconium oxide expressed in terms of total nickel:zirconium is from 0.1 to 100, preferably 0.3 to 20.

The cataloreactant of this invention is characterized by the fact that the size of the nickel crystallites varies from about 50 to 1000 A, preferably 80 to 250 A. If the crystallites are too large the activity of the cataloreactant is too low, and if the crystallites are too small unwanted side reactions take place because of overactivity.

The cataloreactant system of this invention may be prepared by any suitable method. Generally, the system is precipitated from a solution of a nickel and zirconium compound such as the nitrate salt by addition of a solution of a base such as ammonium carbonate, sodium hydroxide, lithium hydroxide, potassium hydroxide, ammonium hydroxide, sodium carbonate, sodium bicarbonate, potassium carbonate and the like and mixtures thereof. Additionally, any nickel or zirconium salt or ester which can react with an oxygen source such as oxygen, water or part of the salt anion to give oxides or hydrous oxides can be used.

After the precipitation of the components of the cataloreactant in the form of the oxide or preferably hydrous oxide, the precipitate is filtered, washed, dried, reduced with hydrogen and exposed to a suitable amount of air or oxygen, or optionally water until the desired oxidation product is achieved. The resulting solid product has a surface area of at least 1.35 square meters per gram, preferably 1.35 to 300 square meters per gram, most preferably 20 to 200 square meters per gram.

In the conditioning operation, the cataloreactant is reduced by being exposed to hydrogen at a temperature between 300°C. and 600°C., preferably 350° to 425°C. The pressure can vary from 0.1 atmosphere to 10 atmospheres and preferably 0.1 to 2 atmospheres of pressure are employed. From about 10% to 90% nickel oxide, and preferably 25% to 60%, is reduced to metallic nickel in this step. The $H_2$ cataloreactant is then oxidized by treatment with a gas containing from about 0.1% to about 21% oxygen, preferably 1% to 5%, at 30°C. to 800°C., preferably 100°C. to 500°C. and at 0.1 atmosphere to 600 atmospheres, preferably for the length of time necessary to achieve a Ni/NiO mole ratio of 0.001 to 10, most preferably 0.01 to 1.

Following this intermediate reduction-oxidation or conditioning step, the cataloreactant is subjected to the ammonia pretreatment. The pretreatment with ammonia raises the effectiveness of the cataloreactant, increases its reactivity and extends its life by adsorbing onto the nickel surfaces and preventing the amination reactants or reaction products from poisoning the nickel. The pretreatment with ammonia can be carried out in several ways. If a batch reactor is used for the subsequent amination reaction, the reactor can be charged with the cataloreactant, sealed, pressurized with ammonia and heated or the reactor can first be heated under a blanket of nitrogen and then a stream of ammonia can be passed over the cataloreactant before introducing the ammonia and aromatic compound.

In a continuous reactor, the ammonia can simply be passed through the conditioned cataloreactant before the start of a new synthesis cycle. For the sake of expediency in either a batch or continuous operation, the ammonia treatment is carried out at the temperature to be used in the subsequent reaction between the ammonia and the aromatic compound. It is to be understood, however, that the ammonia pretreatment can be carried out effectively at from about room temperature (approximately 20°C.) to about 500°C. Preferably, an elevated temperature is employed, most preferably between 250°C. and 400°C. The quantity of ammonia to total nickel in the nickel/nickel oxide of the cataloreactant expressed as part/part on a molar basis ranges from about 0.01 to 20.0, and preferably 0.1 to 2.0.

The time of ammonia pretreatment ranges from about 1 to about 60 minutes, and preferably from about 3 to about 20 minutes.

Pure ammonia can be used in the pretreatment of the cataloreactant. Alternatively, the ammonia can be diluted with inert gases such as nitrogen or helium. Generally there is no advantage in diluting the ammonia.

B. The Amination

The conditions under which the reaction between ammonia and the aromatic compound is carried out depend somewhat on the particular reactants. In general, temperatures of from about 150°C. to about 500°C. and pressures of from about 10 atmospheres to about 1000 atmospheres will be employed.

The amination process may be carried out either batch-wise or in a continuous operation. In a batch-type operation the cataloreactants of this invention are used in such quantities that the weight ratio of the cataloreactant to the aromatic compound is from 0.01 to 10, preferably 0.2 to 3. Any suitable apparatus in which the reactants can be combined and mixed such as an agitated autoclave or a pressure vessel may be used as the reactor. Preferably, the reactor is preheated to the reaction temperature before the amination reactants are introduced. Once the reactor contains the cataloreactant, ammonia and the aromatic compound to be aminated, it is sealed and the reaction is allowed to proceed to the degree of conversion desired. Thereafter, the apparatus and the contents are cooled to room temperature or lower, excess $NH_3$ pressure is vented and the aminated reaction product is separated from unreacted aromatic compound, the cataloreactant and by-products by conventional means such as distillation, crystallization, and the like.

In a continuous operation, the process may be carried out in any suitable apparatus that will permit a contact time between the amination reactants and the cataloreactant of from two seconds to twenty minutes, preferably 30 seconds to 8 minutes. Some such suitable apparatus would include fixed-bed reactors or packed vessels or coils into which the cataloreactant, ammonia and the aromatic compound can be continuously charged and the aromatic compound and ammonia can be passed through a cataloreactant bed. A moving-bed operation may also be employed in which the reaction bed and the reactants either pass concurrently or countercurrently to each other. Still another type of continuous operation which may be employed is a fluidized bed or slurry type in which the cataloreactant composition is carried into the reactor as a slurry in one or more of the reactants.

In either the batch or continuous type of reactor the aromatic compound and the ammonia may be introduced separately or as a single mixed stream. The cataloreactant may be regenerated intermittently or continuously with oxygen or an oxygen-containing gas such as air, optionally with water. If desired, the aromatic compound and ammonia may be reacted in the presence of water.

In the preferred embodiment of this invention, the amination reaction is carried out at a temperature in the range of about 250°C. to about 500°C. and at a pressure ranging from about 30 atmospheres to about 700 atmospheres.

Any aromatic compound with which ammonia is miscible at the temperature and pressure of the reaction and which comes into intimate molecular contact with the cataloreactant of this invention may be directly aminated with ammonia as described herein. By intimate molecular contact is meant that, at the reaction temperature and pressure, the molecules of each reactant are in contact, on a molecular basis, with the cataloreactant of this invention. Some such suitable aromatic compounds include benzene, naphthalene, anthracene, phenanthrene, pyridine, quinoline, isoquinoline, mono- or di- substituted counterparts of any of them and the like, preferably benzene or pyridine.

Other aromatic compounds which may also be aminated in accordance with this invention include those having the formula $(X)_m(Y)_n$ wherein X is benzene or pyridine, m is 1 or 2, n is 0, 1 or 2, and Y is alkyl having one to six carbon atoms such as methyl, ethyl, propyl, butyl, amyl and hexyl, including cycloalkyl such as cyclohexyl and cyclopentyl; halogen such as fluoro and chloro; nitrile; hydroxy; $CONH_2$; alkoxy having one to six carbon atoms such as methoxy, ethoxy, propoxy, butoxy, and hexoxy, including cycloalkoxy such as cyclohexoxy and cyclopentoxy; aryloxy such as phenoxy; amino, including primary, secondary and tertiary amino wherein the secondary amino groups contain alkyl having one to five carbon atoms or aryl such as phenyl; aralkyl such as benzyl, including mono- and dialkylsubstituted aralkyls, wherein the alkyl groups contain one to five carbon atoms such as 2-methyl benzyl, 3-ethylbenzyl, 2,3-dimethylbenzyl and the like; with the proviso that when Y is aryloxy, a secondary or tertiary arylamine or an aralkyl, n is 1. When n is 2, the substituents Y may be the same or different. Any of the substituents Y may be contained on the naphthalene anthracene, phenanthrene, quinoline and isoquinoline nucleus as mentioned above.

Some more specific aromatic compounds which may be aminated directly with ammonia include biphenyl, bipyridine, 4,4'-dichlorobiphenyl, toluene, o-, m- and p-xylene, aniline, cholorobenzene, fluorobenzene, 1,4-di-cholorobenzene, ethylbenzene, anisole, 3-chloropyridine, 4-propylpyridine, hexylbenzene, 4-ethoxypyridine, phenoxy benzene, 4-phenoxypyridine, 3-aminopyridine, dimethylamino benzene, 1,4-diamino benzene, 2,4-diaminopyridine, 4-cyanopyridine, benzamide, benzonitrile, phenetole, o-, m- and p-dimethylbenzene, 1-chloronaphthalene, 2,5-dichloronaphthalene, 1-fluoroanthracene, 2-methylphenanthrene, diphenyl methane, 4-phenyl-2-methyl pyridine, xylyl methylbenzene, 2(bisphenyl)propane, phenoxybenzene, N,N-diethylamino benzene, 4-(N-phenylamino)-pyridine, N-pentylamino benzene, m-phenylenediamine, 3-amido-pyridine, 1-methyl-3-ethyl benzene, o-, m- and p-chloroaniline, o-, m- and p-chlorobenzonitrile, 2-chloro-4-cyanopyridine, p-methoxybenzamide; cyclohexylbenzene, 4-cyclopentylpyridine, 4-(N-methyl-N-phenyl)amino-pyridine, 3-hydroxy-pyridine, 1-hydroxy-3-chlorobenzene, 3-methoxy-quinoline, 5-cyanoisoquinoline, 4,4'-dicyanodiphenyl, 4-hydroxy-4'-fluorobiphenyl, 1,4-dichloroanthracene, 2,7-dihydroxy-phenanthrene, 1-chloro-5-amido-naphthalene, 5-phenoxy-isoquinoline, 3-chloro-4-fluoroquinoline, 2-pentoxy-7-hydroxy phenanthrene, 1-(2,3-dimethylphenyl)-naphthalene, 1,4-dichloronaphthalene, methylisopropylphenanthrene, 9,10-dichloroanthracene, anthradiamine, dihydroanthracene, 2,3-dimethylanthracene, 9-ethylanthracene, aminoquinoline, aminophenylmethyl quinoline, benzoquinoline, chloroquinoline, dimethylquinoline, quinolinol, methoxyquinoline, α-methylquinoline, cyanoquinoline, 1-benzyl-N-methylisoquinoline, N-methyl pyridine, 3-benzylpyridine, 3,5-dimethylpyridine, 4-hydroxypyridine, 3-methyl-5-ethyl-pyridine, 4-propylpyridine, α-naphthylamine, 1-benzylnaphthalene, 1- or 2-chloronaphthalene, any of the naphthalene diamines, naphthalene diols, dichloronaphthalenes, and dimethylnaphthalenes, 1-ethoxynaphthalene, 1- or 2-fluoronaphthalene, isopropylmethylnaphthalene, 1- or 2-ethylnaphthalene, 1-methylisopropylnaphthalene, 1-phenylnaphthalene, naphthamide and the like as well as any other compounds which come within the definition and formula set out hereinbefore which will occur to those skilled in the art.

The preferred aromatic compounds for the amination reaction are benzene and pyridine with the production of aniline and 2-amino pyridine as the preferred objective.

The aromatic amines prepared by the process of this invention are useful in any application in which prior art aromatic amines have been employed such as, for example, in the preparation of isocyanates used to react with polyols in the production of urethanes.

The invention is further illustrated but is not intended to be limited by the following examples, in which all parts and percentages are by weight unless otherwise specified.

EXAMPLE 1

Preparation of Cataloreactant A

Cataloreactant A was prepared by dissolving 1163.2 parts of nickel nitrate and 465.3 parts of zirconyl nitrate in 12 gallons of deionized distilled water. About 465.3 parts of ammonium carbonate were dissolved in 3 gallons of deionized, distilled water. The ammonium carbonate solution was added to the solution of nickelous nitrate and zirconyl nitrate with stirring at the rate of about 35 ml./min. Stirring was stopped and the precipitate was allowed to settle out. The supernatant liquid was decanted off with the precipitate. About 12 gallons of deionized distilled water were stirred into the precipitate and then decanted away. This rinsing procedure was repeated twice more, following which the reaction product was filtered through a thick gel and dried at 120°C. in a non-air-circulating oven for six days. A hard, glassy solid was obtained.

The reaction product was then heated to 400°C. in a quartz tube with a flow of air at 140 cc. per minute for 23 hours to dehydrate it and drive off any nitrogen oxides present. The reaction product was reduced in a stream of nitrogen and hydrogen, each of which was introduced at the rate of 140 cc/min. When the production of water ceased, the reduced mass was cooled to 100°C. while preserving a nitrogen atmosphere by continuing to introduce a nitrogen gas stream at the rate of 140 cc./min. When the temperature reached 100°C., sufficient air was introduced so that the gas stream contained 4% oxygen and these conditions were maintained for 8½ hours. The product was then cooled to room temperature, removed from the apparatus and bottled.

The cataloreactant had the empirical formula Ni/0.3 Zr in which 95% by weight of the nickel was in the form of NiO while all of the zirconium was in the form $ZrO_2$.

EXAMPLE 2

Preparation of Cataloreactant B

Cataloreactant B was prepared by stirring 17 parts of strontium nitrate, 156 parts of zirconyl nitrate and 450 parts of nickelous nitrate into six liters of deionized distilled water until a clear solution was obtained. About 245 parts of ammonium carbonate dissolved in three liters of deionized distilled water were added to the solution of nitrates dropwise over a 2 hour period with stirring. After the addition was complete the stirring was continued for another 90 minutes and then discontinued. The precipitate was allowed to settle out overnight, centrifuged, separated from the supernatant liquid by decantation and then stirred with about 9 liters of water. This procedure was repeated twice more following which the precipitate was filtered under vacuum and allowed to remain on the filter under vacuum overnight. The resulting product was oven-dried at 110°C. for about 24 hours. About 423 parts of dark glassy granules were obtained.

Under atmospheric pressure, 223 parts of the granules thus obtained were hydrogenated in a tube at 380°C. by passing a stream of 85% hydrogen/15% nitrogen at 700 cc./min. for 4 hours (0.057 part hydrogen per part granules). The hydrogenated product was then cooled to 80°C. and oxidized with a stream of 3% oxygen and 97% nitrogen for 16 hours at 150 cc./min., then 1 hour with 5% oxygen and 95% nitrogen at 180 cc./min., and then 1 hour with 7% oxygen and 93% nitrogen at 200 cc./min. The product was then cooled to 25°C. under nitrogen and bottled.

The cataloreactant has the empirical formula Ni/0.25 Zr/0.05 Sr.

EXAMPLES 3–6

About 250 parts of a cataloreactant were loaded into a 1 inch × 36 inch stainless steel reactor. The tube was sealed. The cataloreactant occupied roughly 16 inches in the center of the reactor. The reactor was heated to 350°C. and pressurized to 4500 psig with $N_2$ to check for leaks. The nitrogen pressure was reduced to 500 psig and a mixture of 1½% $O_2$ in $N_2$ was introduced into the reactor at the rate of one cubic ft./min. The percent of $O_2$ and $CO_2$ in the effluent was monitored. When the oxygen level reached 1½% in the effluent (i.e., the same amount being introduced), the oxidation was considered complete; 0.26 moles of NiO were thus prepared and 0.13 moles of oxygen were consumed while 0.003 moles of $CO_2$ were liberated.

The reactor was vented down to atmospheric pressure and purged with ammonia gas at the rate of 200–300 cc./min. for about 5 minutes. The system was pressurized with ammonia to about 150 psig and maintained at from 10 to 30 minutes.

Ammonia and benzene were premixed as shown in the following table in a tank connected to the reactor with a pump. After the system was pressurized to 3500 psig with $N_2$, the pump was activated and the benzene/ammonia mixture was introduced at the rate of 7.8 to 8.5 g. of the mixture per minute.

The table summarizes the results obtained in a series of experiments in which the same cataloreactants were used under substantially the same conditions except that half of the cataloreactants had been conditioned as described above without being subjected to ammonia pretreatment.

As the table clearly indicates, significant improvements in conversion to aniline were obtained when the same cataloreactant was pretreated with ammonia. Indeed, in a preferred embodiment of the invention in which the cataloreactant contained strontium, improvements in conversion of greater than 50% were obtained.

| CATALYST | A | | B | |
|---|---|---|---|---|
| Temperature (°C.) | 350 | 350 | 350 | 350 |
| Pressure (psig) | 7000 | 7000 | 4000 | 4000 |
| Ammonia/Benzene (mole) | 3.0 | 3.0 | 2.36 | 2.95 |
| Cataloreactant Weight | 250 | 250 | 212 | 200 |
| Gas Hourly Space Velocity* | 3.86 | 4.04 | 13.20 | 11.7 |
| Ammonia Treatment | No | Yes | No | Yes |
| Ave. Wt. % Conversion to Aniline | 8.8 | 9.4 | 7.0 | 10.75 |

*Indicates the volume of gas introduced per volume of the reactor containing the cataloreactant.

The nickel/nickel oxide/zirconium oxide cataloreactant system may be used alone or in combination with an oxide or carbonate of another metal such as strontium, barium, calcium, magnesium, zinc, iron, titanium, silicon, aluminum, cerium, thorium, uranium, or of the alkali metals. Combinations with certain clays and the like such as kieselguhr can also be used. The compounds mentioned above may function in the nature of a support or as a promoter for the nickel/nickel oxide/zirconium oxide cataloreactant system. When so used, the oxides or carbonates are added to the cataloreactant preparation as the strontium nitrate was in Example 2 prior to precipitation with ammonium carbonate.

It is to be understood that any of the components and conditions mentioned as suitable herein can be substituted for its counterpart in the foregoing examples and that although the invention has been described in considerable detail in the foregoing, such detail is soley for the purpose of illustration. Variations can be made in the invention by those skilled in the art without departing from the spirit and scope of the invention except as set forth in the claims.

What is claimed is:

1. In a process for aminating an aromatic compound selected from benzene, pyridine and aniline by reaction with ammonia at a temperature of from about 150°C. to about 500°C. and at a pressure of from about 10 to about 1000 atmospheres in the presence of a cataloreactant comprising nickel/nickel oxide/zirconium oxide wherein the ratio of nickel to nickel oxide is from 0.001:1 to 10:1 and the ratio of total nickel to zirconium oxide is from 0.1:1 to 100:1 that was conditioned by (1) reducing in hydrogen from about 10 to 90% of the nickel oxide to metallic nickel and (2) oxidizing with an oxygen containing gas, the improvement which comprises carrying out the reaction in intimate molecular contact with the conditioned cataloreactant which is treated with from about 0.01 to about 20 moles of ammonia per mole of total nickel in the conditioned cataloreactant at a temperature of from about 20°C. to about 500°C. for from about 1 to about 60 minutes prior to introduction to the amination reactants.

2. The process of claim 1 wherein the mole ratio of ammonia/aromatic compound is 0.1:1 to 20:1.

3. The process of claim 1 wherein the aromatic compound is benzene.

4. The process of claim 1 wherein the aromatic compound is aniline.

5. The process of claim 1 wherein the aromatic compound is pyridine.

6. The process of claim 1 where the cataloreactant contains a member selected from the group consisting of oxides and carbonates of strontium, barium, calcium, magnesium, zinc, barium, titanium, aluminum, silicon, cerium, thorium, uranium and the alkali metals.

* * * * *